United States Patent [19]

Steuer et al.

[11] Patent Number: 4,649,120
[45] Date of Patent: Mar. 10, 1987

[54] PROCESS FOR REDUCING TURBIDITY IN CONTROL SERA

[75] Inventors: Dagmar Steuer; Rudolf Schmidtberger, both of Marburg, Fed. Rep. of Germany

[73] Assignee: Behringwerke Aktiengesellschaft, Fed. Rep. of Germany

[21] Appl. No.: 641,589

[22] Filed: Aug. 17, 1984

[30] Foreign Application Priority Data

Aug. 19, 1983 [DE] Fed. Rep. of Germany ....... 3329952

[51] Int. Cl.$^4$ .............................................. G01N 31/00
[52] U.S. Cl. .......................................... 436/13; 436/16
[58] Field of Search ........................................ 436/8–18

[56] References Cited

U.S. PATENT DOCUMENTS

| | | | |
|---|---|---|---|
| 3,260,648 | 7/1966 | Fox | 436/16 |
| 4,127,502 | 11/1978 | LiMutti et al. | 436/16 |
| 4,299,726 | 11/1981 | Crews et al. | 252/408 |
| 4,324,685 | 4/1982 | Louderback | 436/18 |
| 4,358,394 | 11/1982 | Crews et al. | 252/408 |
| 4,363,633 | 12/1982 | Christiansen | 436/16 |
| 4,480,029 | 10/1984 | Dolona | 436/16 |

FOREIGN PATENT DOCUMENTS 1176164 10/1984 Canada .

*Primary Examiner*—John F. Terapane
*Assistant Examiner*—T. J. Wallen
*Attorney, Agent, or Firm*—Finnegan, Henderson, Farabow, Garrett & Dunner

[57] ABSTRACT

A process for reducing turbidity in a dried and redissolved control serum and a dried and reconstituted control serum with reduced turbidity are described. The process can also be applied to control sera for lipid determination, and in particular also to those with an increased lipid content.

3 Claims, No Drawings

PROCESS FOR REDUCING TURBIDITY IN CONTROL SERA

The invention relates to a process for reducing turbidity in a dried and redissolved control serum and to a dried control serum with reduced turbidity after resolution. The process is also suitable for control sera for lipid determinations, especially those with an increased lipid content.

Control sera are to be understood as sera of human or animal origin which have an optionally modified, but serum-like composition, contain serum constituents in a known concentration and are suitable for the control of determination methods for these serum constituents.

Processes for the preparation of such control sera, including the adjustment of individual constituents to desired concentrations, are known.

In order to ensure the storage stability of unstable components, such as, for example, enzymes or lipoproteins, control sera can be lyophilized and stored at a low temperature. Undesirable side effects of lyophilization are turbidity phenomena, which occur after reconstitution of the control sera by a change in the solution properties, especially of the lipoproteins. These turbidity phenomena frequently interfere in spectrophotometric methods, so that a sample blank value is additionally required. Turbidity presents particular problems in measurements in the region of 340 nm, in which those enzyme activity determinations based on NADH/NAD measurement are chiefly carried out. The extinction of NADH, which is already high per se, is increased further by the turbidity, so that it frequently has to be measured in a range in which precise measurements are not possible. The results become more inaccurate and greatly depend on the quality of the photometer.

Processes are already known for avoiding turbidity phenomena. Shock freezing (German Offenlegungsschrift No. 2,243,014) requires a great deal of technological effort.

The use of purified lipid fractions (literature: Clin. Chem. 22, (1976), 456–490 and 1299–1305) causes high raw materials costs, and the addition of detergents may interfere with the particular test. Addition of sugars, sugar-alcohols or amino-sugars (German Pat. No. 2,825,391, Research Disclosure October 1977, No. 16, 229, Clinical Abstracts, volume 87, 1977, No. 196,807 g and volume 90, 1979, No. 511 11c) causes a high viscosity and interferes with glucose determination methods. The addition of organic substances which are not sugar-like, such as methanol, alanine, triethylene glycol, valine, acetate, lactate or sodium 2-hydroxymethylbutyrate (German Pat. No. 3,107,060) can lead to interference in enzyme reactions in the case of alanine and methylbutyrate. Addition of methanol generally constitutes a health hazard; if sodium acetate is used, the control serum can no longer be used as a universal control serum for electrolyte determinations; addition of ammonium compounds interferes in urea determinations; other substances can cause general test interferences.

The invention was therefore based on the object of preparing a universal control serum, and in particular a lipid control serum, which has a reduced tendency towards turbidity after reconstitution of a dried form and does not have the disadvantages described for the known processes.

Surprisingly, it has been found that reconstituted control sera of relatively low turbidity can be prepared if proline is added to the control serum before drying.

It has furthermore been found that turbidity as a result of added lipids, in particular triglycerides, is further reduced by combination of the aminoacid mentioned with Na deoxycholate, especially if the control serum has a reduced electrolyte content (is low in electrolyte). Na deoxycholate is particularly suitable for this purpose because it does not itself cause interfering turbidity.

The invention thus relates to a process for reducing turbidity in a dried and reconstituted control serum, which comprises adding proline to the control serum.

A particular embodiment of the invention comprises also adding Na deoxycholate to a control serum with an increased lipid content. This is particularly advantageous if the ionic strength of the control serum is low, that is to say if it has a low electrolyte content.

The effective concentration of the above aminoacid is between 5 and 100 g/liter, the amount required depending on the lipid content of the serum. Sodium deoxycholate is used in a concentration of 0.5–5 g/liter.

"Low in electrolytes" in the context of the present invention means that the concentration of sodium is 40 to 80 mmols/liter and that of chloride ions is 20 to 70 mmols/liter. The process according to the invention is suitable for the preparation of clinical-chemical control sera, i.e. products which are to be used for the quality control of clinically useful serum parameters, such as the enzyme, substrate, metabolite, hormone or electrolyte content. It is also suitable for the preparation of a particular lipid control or a lipid calibrator. The reduction in the turbidity is measured as follows: the extinction of the dried control serum reconstituted with distilled water and containing one or both of the additives according to the invention was measured with a light path of photometer at 546 nm in a cell with a layer thickness of 1 cm and was compared with the extinction of the same control serum without the addition.

Reconstitution is understood as meaning the solution of a dried material in the amount of solvent which it contained before drying.

The following examples illustrate the invention.

EXAMPLES

Pooled human serum from healthy donors or human serum with a reduced NaCl content was used as the serum base of the control serum. Egg yolk extract was added to increase the triglyceride concentration. Cholesterol was added as bovine cholesterol concentrate. Proline and, if appropriate, Na deoxycholate were then added in the concentration shown, and the mixture was then filtered free from germs, filled into bottles and lyophilized. After reconstitution with distilled water, the turbidity was measured.

The following table shows the results of the extinction measured at 546 nm.

| Basis material | Cholesterol (mmol/liter) | Triglyceride (mmol/liter) | Na deoxychloate (g/liter) | Proline (g/liter) | Extinction 546 nm |
|---|---|---|---|---|---|
| Normal serum* | 3.1 | 0.91 | 0 | 0 | 0.616 |
|  | 3.1 | 0.91 | 0 | 35 | 0.383 |
|  | 3.1 | 0.91 | 0 | 115 | 0.139 |
|  | 4.91 | 0.91 | 0 | 0 | 1.100 |
|  | 4.91 | 0.91 | 0 | 50 | 0.602 |

-continued

| Basis material | Cholesterol (mmol/ liter) | Tri- glyceride (mmol/ liter) | Na deoxychloate (g/liter) | Proline (g/ liter) | Extinc- tion 546 nm |
|---|---|---|---|---|---|
|  | 4.91 | 0.91 | 2 | 50 | 0.200 |
|  | 7.76* | 0.91 | 2 | 50 | 0.265 |
|  | 5.69* | 2.29* | 2 | 0 | 1.035 |
|  | 5.69* | 2.29* | 2 | 50 | 0.614 |
|  | 7.76* | 2.29* | 2 | 0 | 1.304 |
|  | 7.76* | 2.29* | 2 | 10 | 1.219 |
|  | 7.76* | 2.29* | 2 | 50 | 0.728 |
| Serum low in electro- lytes | 4.58 | 0.67 | 0 | 0 | 0.450 |
|  | 8.53* | 3.49* | 0 | 0 | >3 |
|  | 8.53* | 3.49* | 2 | 50 | 0.6–0.8 |
|  | 11.4* | 5.28* | 0 | 0 | >3 |
|  | 11.4* | 5.28* | 2 | 50 | 0.7–0.8 |

*The concentrations thus labelled were obtained by addition of cholesterol or triglycerides.

We claim:

1. A process for reducing turbidity in a dried and reconstituted control serum, which comprises adding proline and Na deoxycholate to the control serum before drying wherein the concentration of the proline in the liquid control serum is 5–100 g/liter and the concentration of Na deoxycholate in the liquid control serum is 0.5–5 g/liter.

2. The process as claimed in claim 1, wherein the concentration of sodium in the liquid control serum is 40–80 mmols/liter and that of the chloride ions is 20–70 mmols/liter.

3. A control serum in dry form, which contains proline and Na deoxycholate wherein the concentration of the proline in the liquid control serum before drying is 5–100 g/liter and the concentration of Na deoxycholate in the liquid control serum before drying is 0.5–5 g/liter.

* * * * *